United States Patent
Wulfert et al.

(10) Patent No.: US 7,718,639 B2
(45) Date of Patent: May 18, 2010

(54) 7-HYDROXYEPIANDROSTERONE HAVING NEUROPROTECTIVE ACTIVITY

(75) Inventors: Ernst Wulfert, Brussels (BE); Ashley Ker Pringle, Southampton (GB); Lars Eric Sundstrom, Old Alresford (GB)

(73) Assignee: Hunter-Fleming Limited, Dorset (GB)

( * ) Notice: Subject to any disclaimer, the term of this patent is extended or adjusted under 35 U.S.C. 154(b) by 844 days.

(21) Appl. No.: 10/312,533

(22) PCT Filed: Jun. 29, 2001

(86) PCT No.: PCT/GB01/02937

§ 371 (c)(1),
(2), (4) Date: Mar. 26, 2003

(87) PCT Pub. No.: WO02/00225

PCT Pub. Date: Jan. 3, 2002

(65) Prior Publication Data

US 2003/0166626 A1    Sep. 4, 2003

(30) Foreign Application Priority Data

Jun. 29, 2000  (GB) ................................ 0016022.6

(51) Int. Cl.
*A61K 31/56* (2006.01)
(52) U.S. Cl. ..................................................... 514/178
(58) Field of Classification Search ................ 514/182
See application file for complete search history.

(56) References Cited

U.S. PATENT DOCUMENTS

| | | | |
|---|---|---|---|
| 4,011,314 A | 3/1977 | Petzoldt et al. | |
| 5,212,167 A | 5/1993 | Farb et al. | |
| 5,387,583 A * | 2/1995 | Loria | 514/171 |
| 5,554,601 A | 9/1996 | Simpkins et al. | |
| 5,556,847 A | 9/1996 | Johnson et al. | |
| 5,707,983 A | 1/1998 | Lardy | |
| 5,763,433 A | 6/1998 | Morfin | |
| 5,925,630 A | 7/1999 | Upasani et al. | |
| 5,976,850 A | 11/1999 | Lathe et al. | |
| 5,985,242 A | 11/1999 | Findeis et al. | |
| 6,172,088 B1 * | 1/2001 | Simpkins et al. | 514/340 |
| 6,407,084 B2 | 6/2002 | Dray | |
| 6,420,353 B1 | 7/2002 | Lathe et al. | |
| 6,667,299 B1 | 12/2003 | Ahlem et al. | |

2003/0083231 A1    5/2003  Ahlem et al.

FOREIGN PATENT DOCUMENTS

| | | | |
|---|---|---|---|
| GB | 1528796 | | 10/1978 |
| GB | 2317826 | | 8/1998 |
| WO | 94/03176 | | 2/1994 |
| WO | WO 94/03176 | * | 2/1994 |
| WO | 94/20111 | | 9/1994 |
| WO | WO 95/12402 | | 5/1995 |
| WO | WO 96/40152 | | 12/1996 |
| WO | WO 97/03677 | | 2/1997 |
| WO | 97/37664 | | 10/1997 |
| WO | WO 97/37664 | * | 10/1997 |
| WO | 98/08868 | | 3/1998 |
| WO | WO 98/22113 | | 5/1998 |
| WO | WO 98/43647 | | 10/1998 |
| WO | WO 98/48812 | * | 11/1998 |
| WO | WO 99/15179 A1 | | 4/1999 |
| WO | 99/24400 | | 5/1999 |
| WO | WO 99/26630 | | 6/1999 |
| WO | WO 99/31049 | | 6/1999 |
| WO | WO 99/52532 | * | 10/1999 |
| WO | WO 00/30652 | | 6/2000 |
| WO | 01/32680 | | 5/2001 |
| WO | 01/60375 | | 8/2001 |
| WO | WO 02/00224 | | 1/2002 |

OTHER PUBLICATIONS

"7-Hydroxylated epiandrosterone (7-0H-EPIA) reduces ischaemia-induced neuronal damage both in vivo and in vitro," Ashley K. Pringle, et al.; European Journal of Neuroscience, vol. 18 pp. 117-124, 2003.

*Curriculum Vitae* of Dr. Douglas F. Covey (Exhibit 1 of the Declaration of Dr. Douglas F. Covey), 2008.

Covey, D. F. et al., 1979, "19-Acetylenic, 19-Hydroxy-Androst-4-ene-3,17-diones. Potential Suicide Substrates of Estrogen Biosynthesis," *Tetrahedron Lett.*, No. 23, 2105-2108 (Exhibit 2 of the Declaration of Dr. Douglas F. Covey).

Covey, D. F. et al., 1981, "10β-Propynyl-substituted Steroids: Mechanism-based Enzyme-activated Irreversible Inhibitors of Estrogen Biosynthesis," *J. Biol. Chem.* 256(3):1076-1079 (Exhibit 3 of the Declaration of Dr. Douglas F. Covey), Abstract only.

Covey, D. F. et al., 1982, "Inhibitors of Steroid Biosynthesis: Preparation of 5,10-Secoestr-4-ynes," *J. Org. Chem.*, 47, 5315-5318 (Exhibit 4 of the Declaration of Dr. Douglas F. Covey).

(Continued)

*Primary Examiner*—Barbara P Badio
(74) *Attorney, Agent, or Firm*—Dechert LLP

(57) ABSTRACT

7-Hydroxyepiandrosterone may be used for protection against acute or chronic neuronal damage.

9 Claims, 3 Drawing Sheets

OTHER PUBLICATIONS

Hu, Y. et al., 1993, "Synthesis of 1,10-Seco-5α-estr-1-ynes: Potential Mechanism-based Inhibitors of 3α- and 3β-Hydroxysteroid Dehydrogenases," *J. Chem. Soc., Perkins Trans* 1:417-422 (Exhibit 5 of the Declaration of Dr. Douglas F. Covey).

Beusen, D. et al., 1986, "Role of Substrate Conformational Features in the Stereospecificity of Aromatase," *Biochemistry* 25:662-667 (Exhibit 6 of the Declaration of Dr. Douglas F. Covey).

Hu Y. et al., 1993, "Neurosteroid Analogues: Structure-Activity Studies of Benz[e]indene Modulators of $GABA_A$ Receptor Function. 1. The Effect of 6-Methyl-Substitution on the Electrophysiological Activity of 7-Substituted Benz[e]indene-3-carbonitriles," *J. Med. Chem.*, 36(24):3956-3967 (Exhibit 7 of the Declaration of Dr. Douglas F. Covey).

Hu Y. et al., 1995, "Neurosteroid Analogues. 2. Total Synthesis and Electrophysiological Evaluation of Benz[e]indene Analogues of the Anesthetic Steroid Alphaxalone," *J. Org. Chem.*, 60: 3619-3625 (Exhibit 8 of the Declaration of Dr. Douglas F. Covey).

Scaglione, J. et al., 2006, "Neurosteroid Analogues. 11. Alternative Ring System Scaffolds: γ-Aminobutyric Acid Receptor Modulation and Anesthetic Actions of Benz[f]indenes," *J. Med. Chem.*, 49(15):4595-4605 (Exhibit 9 of the Declaration of Dr. Douglas F. Covey).

Wang, C. et al., 2007, "Neurosteroid Analogues. Part 13. Synthetic Methods for the Preparation of 2β-Hydroxygonane Derivatives as Structural Mimics of *ent*-3α-*Hydroxysteroid Modulators of* $GABA_A$ *Receptors*," *Tetrahedron* 63:7977-7984 (Exhibit 10 of the Declaration of Dr. Douglas F. Covey).

Green, P.S. et al., 2001, "The Nonfeminizing Enantiomer of 17β-Estradiol Exerts Protective Effects in Neuronal Cultures and a Rat Model of Cerebral Ischemia," *Endocrinology*, 142(1):400-406 (Exhibit 11 of the Declaration of Dr. Douglas F. Covey).

Perez, E. et al., 2005, "Neuroprotective Effects of an Estratriene Analog are Estrogen Receptor Independent In Vitro and In Vivo," *Brain Res.*, 1038, 216-222 (Exhibit 12 of the Declaration of Dr. Douglas F. Covey).

Wang, X. et al., 2006, "Neuroprotective Effects of 17β-Estradiol and Nonfeminizing Estrogens against $H_2O_2$ Toxicity in Human Neuroblastoma SK-N-SH Cells," *Mol. Pharmacol.*, 70(1):395-404 (Exhibit 13 of the Declaration of Dr. Douglas F. Covey).

Wittmer, L. et al., 1996, "Enantioselectivity of Steroid-induced γ—Aminobutyric $Acid_A$ Receptor Modulation and Anesthesia," *Mol. Pharmacol.* 50(6):1581-1586 (Exhibit 14 of the Declaration of Dr. Douglas F. Covey).

Li, W. et al., 2006, "Enantiomers of Neuroactive Steroids Support a Specific Interaction with the GABA-C Receptor as the Mechanism of Steroid Action," *Mol. Pharmacol.* 69(6):1779-1782 (Exhibit 15 of the Declaration of Dr. Douglas F. Covey).

Akwa, Y. et al., 2001, "The Synthetic Enantiomer of Pregnenolone Sulfate is very Active upon Memory in Rats and Mice, Even More so than its Physiological Neurosteroid Counterpart: Distinct mechanisms?," *Proc. Natl. Acad. Sci.* 98(24):14033-14037 (Exhibit 16 of the Declaration of Dr. Douglas F. Covey).

Crowder, C. M. et al. 2001, "Enantiospecificity of Cholesterol Function in Vivo," *J. Biol. Chem.*, 276(48):44369-44372 (Exhibit 17 of the Declaration of Dr. Douglas F. Covey).

Westover, E J. et al., 2003, "Cholesterol Depletion Results in Site-specific Increases in Epidermal Growth Factor Receptor Phosphorylation due to Membrane Level Effects," *J. Biol. Chem.* 278 (51):51125-51133 (Exhibit 18 of the Declaration of Dr. Douglas F. Covey).

Rose, K. et al., 1997, "Cyp7b, a Novel Brain Cytochrome P450, Catalyzes the Synthesis of Neurosteroids 7α-Hydroxy Dehydroepiandrosterone and 7α-Hydroxy Pregnenolone," *Proc. Natl. Acad. Sci.* 94:4925-4930 (Exhibit 23 (numbered out of order) of the Declaration of Dr. Douglas F. Covey).

Akwa, Y. et al., 1993, "Astrocytes and Nureosteroids: Metabolism of Pregnenolone and Dehydroepiandrosterone. Regulation by Cell Density," *J. Cell Biology*, vol. 121, No. 1, pp. 135-143.

Akwa, Y. et al., 1992, "Neurosteroid Matabolism: 7α-Hydroylation of Dehydroepiandrosterone and Pregnenolone by Rat Brain Microsomes," *Biochem. J.* 288, 959-964.

Dean, P. D. G. et al., 1971, "Preparation of 17β-Oestradiol-6-(0-Carboxymethyl) Oxime-Bovine Serum Albumin Conjugate," *Steroids*, 18:593-603.

Dichter, M., 1973, "Rat Cortical Neurons in Cell Culture: Culture Methods, Cell Morphology, Electrophysiology, and Synapse Formation," *Brain Res* 149, 279-293.

Doostzadeh, J. et al.,1998, "Inhibition Studies of Dehydroepiandrosterone 7α and 7β-hydroxylation in Mouse Liver Miscrosomes," *Steroids* 63, 608-614.

Dubal, D. et al., 1999, "Estradiol Modulates bcl-2 in Cerebral Ischemia: A Potential Role for Estrogen Receptors," *J. Neurosci* 19 (15): 6385-6389.

Durkin, J. P. et al., 1996, "An Early Loss in Membrane Protein Kinase C Activity Precedes the Excitatory Amino-Acid Induced Death of Primary Cortical Neurons," *J. Neurochem* 66, 951-962.

Fieser, L. F. et al., 1967, *"Reagents for Organic Synthesis"*, vol. 1,819-820.

Gill, J. et al., 1989, "Improved Preparation of 3,17s-Dihydroxyoestra-1,3,5(10),6-Tetraene," *Synth. Commun.*19 (1&2), 155-158.

Guiraud, J. M. et al., 1979, "Pituitary Metabolism of 5α-Androstane-3β-17β-Diol : Intense and Rapid Conversion into 5α-Androstane-3β, 6α, 17β,-Triol and 5α-Androstane-3β, 7α, 17β-Triol," *Steroids* 34 (3) 241-248.

Holler, M. et al., 1984, "Disposition of [4-14c]oestradiol-17β in the Isolated Perfused Brain of the Rat," *J. Steroid Biochem*, 20(3) 785-787.

International Preliminary Examination Report for PCT/GB01/02929 dated May 13, 2002.

International Preliminary Examination Report for PCT/GB01/00627 dated Aug. 9, 2002.

International Preliminary Examination Report for PCT/GB01/02937 dated May 13, 2002.

International Search Report for PCT/GB01/00627 mailed Aug. 23, 2001.

International Search Report for PCT/GB01/02929 mailed Nov. 14, 2001.

International Search Report for PCT/GB01/02937 mailed Nov. 29, 2001.

Iriarte, J. et al., 1958, "Steroids. XCIX. Synthesis of Ring B Oxygenated Estrogens," *J. Am. Chem. Soc.*, 80 (22), 6105-6110.

Irwin, R. et al., 1994, "Steroid Potentiation and Inhibition of N-Methyl-D-aspartate Receptor-Mediated Intracellular Ca++ Responses: Structure-Activity Studies" *J. Pharmacol. Exp. Ther.* 271(2), 677-82.

Muller, R. E. et al., 1977,"Post-Coital Contraceptive Activity and Estrogen Receptor Binding Affinity of Phenolic Steroids," *Endo* 100(2):513-519.

Office Action for U.S. Appl. No. 10/203,880 mailed on Feb. 10, 2004.
Office Action for U.S. Appl. No. 10/203,880 mailed on Sep. 3, 2004.
Office Action for U.S. Appl. No. 10/312,523 mailed on Jul. 1, 2004.
Office Action for U.S. Appl. No. 10/312,523 mailed on Feb. 28, 2005.
Office Action for U.S. Appl. No. 10/312,523 mailed on Dec. 21, 2005.
Office Action for U.S. Appl. No. 10/312,523 mailed on Mar. 26, 2007.
Office Action for U.S. Appl. No. 10/312,523 mailed on Jan. 14, 2008.

Park-Chung, M. et al., 1997, "Distinct Sites for Inverse Modulation of N-Methyl-D-Aspartate Receptors by Sulfated Steroids" *Mol. Pharmacol.* 52: 1113-1123.

Peters, R. H. et al., 1989, "17-Desoxy Estrogen Analogs," *J Med Chem*. 32(7):1642-52.

Pons, M. et al., 1978, "Structural Requirements for Maximal Inhibitory Allosteric Effect of Estrogens and Estrogen Analogues on Glutamate Dehyrogenase," *Eur. J. Biochem*, 84, 257-266.

Pringle, A. K. et al., 1997, "Neuroprotection by both NMDA and Non-NMDA Receptor Antagonists in In Vitro Ischemia," *Brain Research* 755 36-46.

Pringle, A. K. et al., 1996, "Selective Type N-Type Calcium Channel Antagonist Omega Conotoxin MVIIA is Neuroprotective Against Hypoxic Neurodegeneration in Organotype Hippocampal-Slice Cultures," *Stroke* 27(11):2124-2130.

Schneider, J. J. et al., 1959, "Fractionation and Isolation of Steroid Conjugates," *Recent Progr. Horm. Res.* 15:201-230.

Steraloids Inc., Wilton, New Hampshire, estra-1,3,5(10),6-tetraene-3, 17J3diol diacetate (cat. No. E475), 2008.

Takanashi, K. et al., 1995, "On the Inhibitory Effect of $C_{17}$-Sulfoconjugated Catechol Estrogens upon Lipid Peroxidation of Rat Liver Microsomes," *Biol. Pharm. Bull* 18(8) 1120-1125.

Warner, M. et al., 1989,"Distribution and Regulation of 5α-Androstane-3β,17β-Diol Hydroxylase in the Rat Central Nervous System," *Endocrinology* 124 (6), 2699-2706.

Wiese, T. et al., 1997, "Introduction of the Estrogen Specific Mitogenic Response of MCF-7 Cells by Selected Analogues of Estrtadiol-17β: A 3D QSAR Study," *J. Med. Chem.* 40, pp. 3659-3669.

Zaulyanov, L. et al., 1999, "Glutamate Receptor Requirement for Neuronal Death from Anoxia-Reoxygenation: An in vitro Model for Assessment of the Neuroprotective Effects of Estrogen," *Cellular and Molecular Neurobiology* 19(6): 705-718.

Ashley K. Pringle, et al., "7-hydroxylated epiandrosterone (7-OH-EPIA) reduces ischaemia-induced neuronal damage both in vivo and in vitro", European Journal of Neuroscience, Apr. 30, 2003, pp. 117-124, vol. 18.

"Investigation of HF0220 efficacy in a model of superoxide-medicated toxicity", Capsant Neurotechnologies, May 22, 2003, 4 pages.

"Neuroprotective efficacy of HF0220 against β-amyloid fragment 1-42 toxicity", Capsant Neurotechnologies, Jul. 17, 2003, 6 pages.

"Protective effect of HF0220 against Ischaemia in PC-12 cells", Capsant Neurotechnologies, May 22, 2006, 7 pages.

Bertalan Dudas, et al., "Protection against inflammatory neurodegeneration and glial cell death by 7β-hydroxy epiandrosterone, a novel neurosteroid", Neurobiology of Disease, 2004, pp. 262-268, vol. 15.

V. Chmielewski, et al., "Dexamethasone-Induced Apoptosis of Mouse Thymocytes: Prevention By Native 7a-hydroxysteroids", pp. 238-246, Immunology and Cell Biology, vol. 78, No. 3, 2000.

The Merck Index (2001) (http://themerckindex.cambridgesoft.com), monograph Nos. 03738, 03640, 07822 and 03743.

C.M.P. Rodrigues, et al., "Amyloid.beta.-Peptide Disrupts Mitochondrial Membrane Lipid and Protein Structure: Protective Role of Tauroursodeoxycholate", Biochem. Biophys. Res. Commun., vol. 281. No. 2, 2001, pp. 468-474, XP001019285, Figs. 1-4.

STN/CAS online, file Biosis, Acc. No. 1999:496516 (Silva et al. "Excitotoxic neuronal death may explain bilirubin toxicity and is prevented by ursodeoxycholic acid". Hepatology (Oct. 1999), vol. 30, No. 4, Part 2, 386A), Abstract.

Covey, D. F. et al., 1981, "10β-Propynyl-substituted Steroids: Mechanism-based Enzyme-activated Irreversible Inhibitors of Estrogen Biosynthesis," *J. Biol. Chem.* 256(3):1076-1079 (Exhibit 3 of the Declaration of Dr. Douglas F. Covey).

Office Action for U.S. Appl. No. 10/312,523 mailed on Jun. 19, 2009.

U.S. Appl. No. 60/126,056, filed Mar. 23, 1999.

IUPAC-IUB Joint Commission on Biochemical Nomenclature (JCBN), "The nomenclature of steroids—Recommendations 1989," *Eur. J. Biochem.* 186, 429-458.

* cited by examiner

7-HYDROXYEPIANDROSTERONE HAVING NEUROPROTECTIVE ACTIVITY

This application is a 371 of PCT/GB01/2937 filed Jun. 29, 2001

The present invention relates to the use of certain 7-hydroxy-steroid compounds for protection against neuronal cell death, and which are thus useful in the treatment and prevention of such conditions or the sequelae of such conditions as Alzheimer's Disease, Parkinson's Disease, Cognitive Impairment No Dementia (CIND), stroke, brain trauma, spinal cord injury and peripheral nerve injury, it is also useful for enhancing cognitive function.

The production of 7α-hydroxylated metabolites of dehydroepiandrosterone (DHEA) in vivo has been known since 1959 with the identification of 7α-hydroxy-DHEA in urine [J J Schneider, M L Lewbart, Recent Progr. Horm. Res. 15 (1959) 201-230; L Starka et al, Clin. Chim. Acta 7 (1961) 309-316)]. Since then, extensive 7α-hydroxylation of 3β-hydroxysteroid substrates (including DHEA and epiandrosterone—EPIA) has been reported in tissue preparations from many human organs, including adult and foetal liver, testes, epididymus, skin, mammary tissue, prostate, adipose stromal cells and tonsils. Hydroxylation of DHEA at the 7-position has also been demonstrated in rat liver and in numerous mouse tissues and organs. In all these studies, 7α-hydroxy-DHEA was by far the major metabolite produced. Indeed, Doostzadeh et al [Steroids 63 (1998) 608-614] reported that the production rate of 7α-hydroxy-DHEA by mouse liver microsomes was more than fifteen times the production rate of 7β-hydroxy-DHEA.

EPIA, DHEA and pregnenolone have also been shown to be rapidly and extensively transformed to their corresponding 7α-hydroxy metabolites in the rat brain [J M Guiraud et al, Steroids 34 (1979) 241-248; M Warner et al, Endocrinology 124 (1989) 2699-2706; Y Akwa et al, Biochem. J. 288 (1992) 959-964)].

WO97/37664 discloses the use of certain specific compounds, including 7α-hydroxy-substituted steroids, to treat neuropsychiatric, immune or endocrine disorders. Among the disorders suggested in WO97/37664 that these compounds may be used to treat is included Alzheimer's Disease. However, the mechanism suggested for this action is that the disorder is hypothesised to result from a deficit of the 7α-hydroxy-substituted steroid in the brain, and the treatment proposed in WO97/37664 thus rectifies this deficit by the administration of a 7α-hydroxy-substituted steroid to replace the missing compound. The procedure described in WO97/37664 thus treats an existing condition, rather than preventing the condition or preventing a worsening of the condition by preventing further neuronal damage. WO97/37664 does not, therefore, describe a neuroprotective effect. It also does not suggest that the compounds may be used to prevent the damage caused by sudden and traumatic events such as stroke.

BRIEF DESCRIPTION OF THE DRAWINGS

FIG. 1A, the data are presented as mean number±SEM of intact neurons per 400 μm length of CA1 region.

FIG. 1B, the data are expressed as percentage of intact neurons per 400 μm length of CA1 region compared to sham operated animals set as 100%.

FIG. 1C, the data are presented as absolute percentage of neuroprotection when the number of surviving neurons in the ischemia group was set to zero and those of the sham operated group was set to 100%.

Figure 1A:
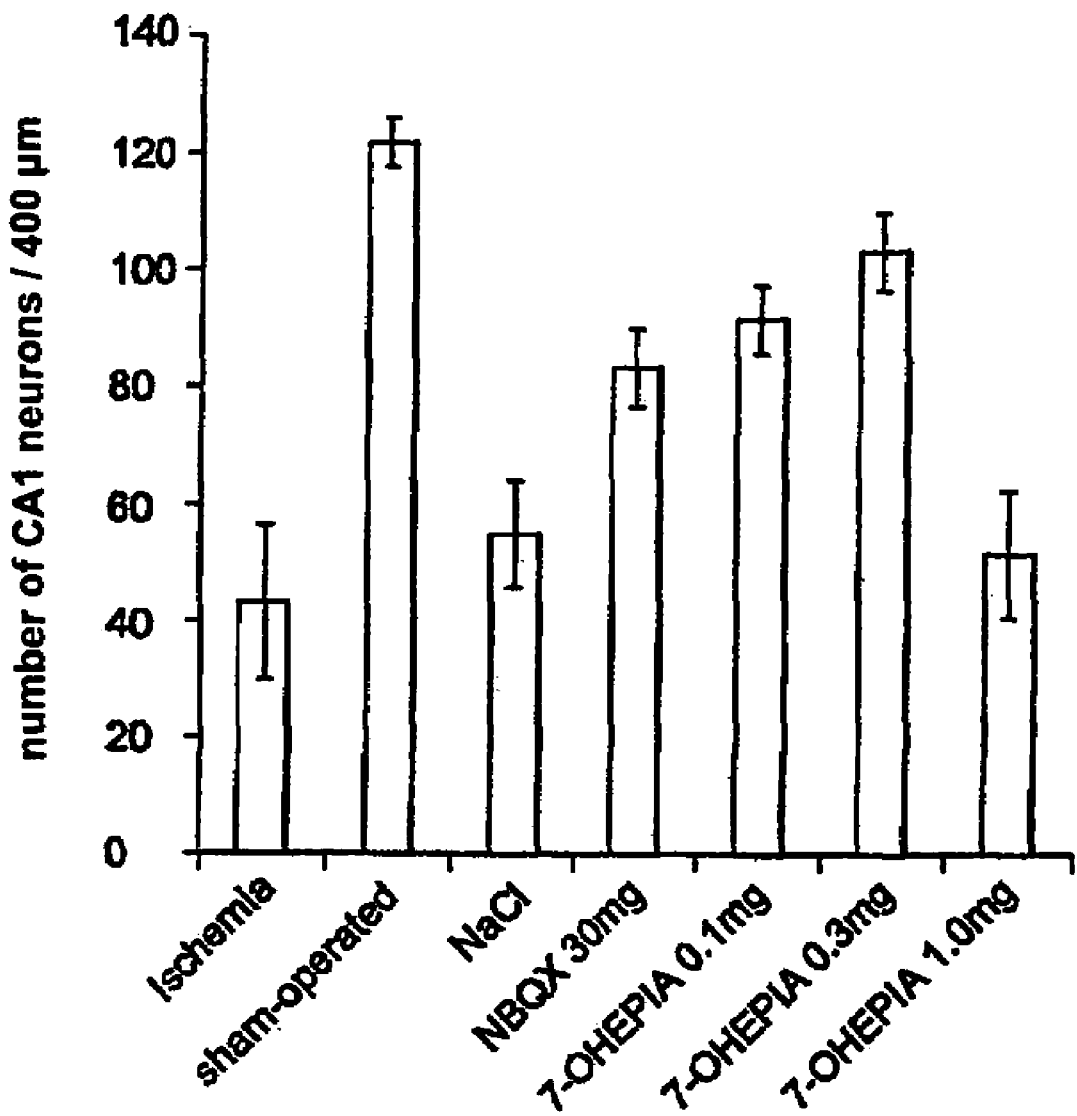
FIGS. 1A, 1B and 1C show graphs representing the number of morphological intact hippocampal CA1 pyramidal cells 7 days after global cerebral ischemia in rats and under the influence of different compounds.

We have now surprisingly discovered that 7-hydroxy-epiandrosterone, whether α, β or a mixture, can be used to protect against acute and chronic neuronal damage caused by such events as stroke, brain trauma and cerebral ischaemia such as may be induced by sub-arachnoid haemhorrage or which occurs during heart bypass surgery etc.

In events such as prolonged hypoxia and ischaemia, which may or may not be associated with hypoglycaemia, neuronal damage, to varying degrees, is encountered.

Ischaemia typically occurs during heart attacks, but the damage incurred at these times is substantially limited to the heart tissues, and certain treatments have been developed. With regard to the present invention, we are concerned with the effects of more long term ischaemia on the brain, such as occurs with stroke patients or as a result of head injury. The severity of the ischaemia depends on the nature of the stroke or injury, but, invariably, there is brain damage, and it is this which the present invention addresses.

Various neuroprotective agents are known in the art which attempt to alleviate the problem of brain damage, but all of those currently known tend to be associated with adverse side effects. For example, MK801 (dizocilpine maleate) is a fairly simple molecule and is known to provide a level of neuroprotection to ischaemic patients. However, MK801 is also associated with "alarming psychotropic effects" (Martindale), as well as adverse motor effects. The neuroprotective effects are detailed in Brain Research 755 (1997) 3646 (Pringle, A. K., et al), incorporated herein by reference. These same authors also described the neuroprotective effects of conotoxin in an earlier paper but, despite the neuroprotective effects of this compound, adverse side effects, in vivo, are observed.

Thus, the present invention consists in the use for the manufacture of a medicament for protection against acute or chronic neuronal damage of 7-hydroxyepiandrosterone (7-hydroxy-EPIA).

This compound may be represented by the formula (I):

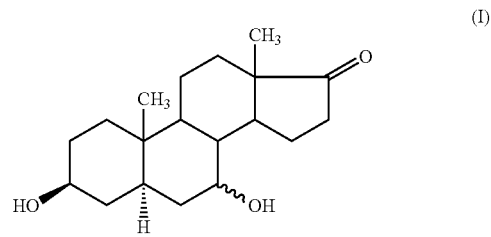

and the 7α and 7β isomers are, respectively:

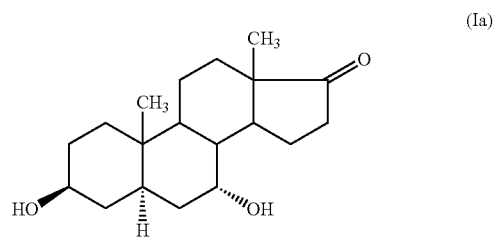

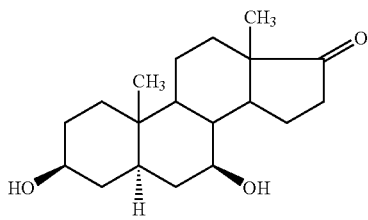

The invention also embraces the use of precursors of these compounds and compounds which, in vivo, are metabolised to give these compounds.

The α and β isomers may be used alone or in admixture, and, if in admixture, may be present in any proportions. However, the 7β-isomer appears to show greater activity and is therefore presently preferred.

The compounds of the present invention may be prepared by a variety of processes, well known in themselves, starting from the parent steroids. For example, they may be prepared by the methods described in the literature referred to above, which would give a mixture of the 7β and corresponding 7α compounds, which may then be separated by well known techniques.

As an example, 7α and/or 7β-hydroxy EPIA may be obtained from DHEA by allylic oxidation after protection of the 3β-hydroxy group and the 17-ketone group using conventional methods. The product is then reduced with a soluble metal compound catalyst (such as sodium hydride) and the 3β-hydroxy and 17-ketone groups are deprotected. The 7α-hydroxy and 7β-hydroxy epimers may then, if desired, be separated by conventional means, for example column chromatography, and the 7α- and 7β-hydroxy EPIA may be crystallised to purity.

Alternatively, 7α- and 7β-hydroxy-EPIA may be prepared as illustrated by the following reaction scheme:

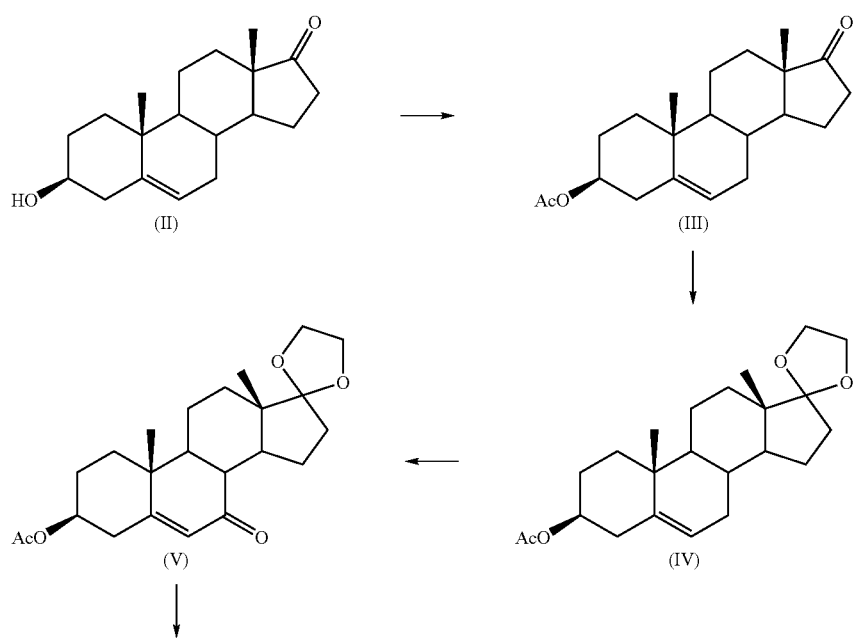

-continued

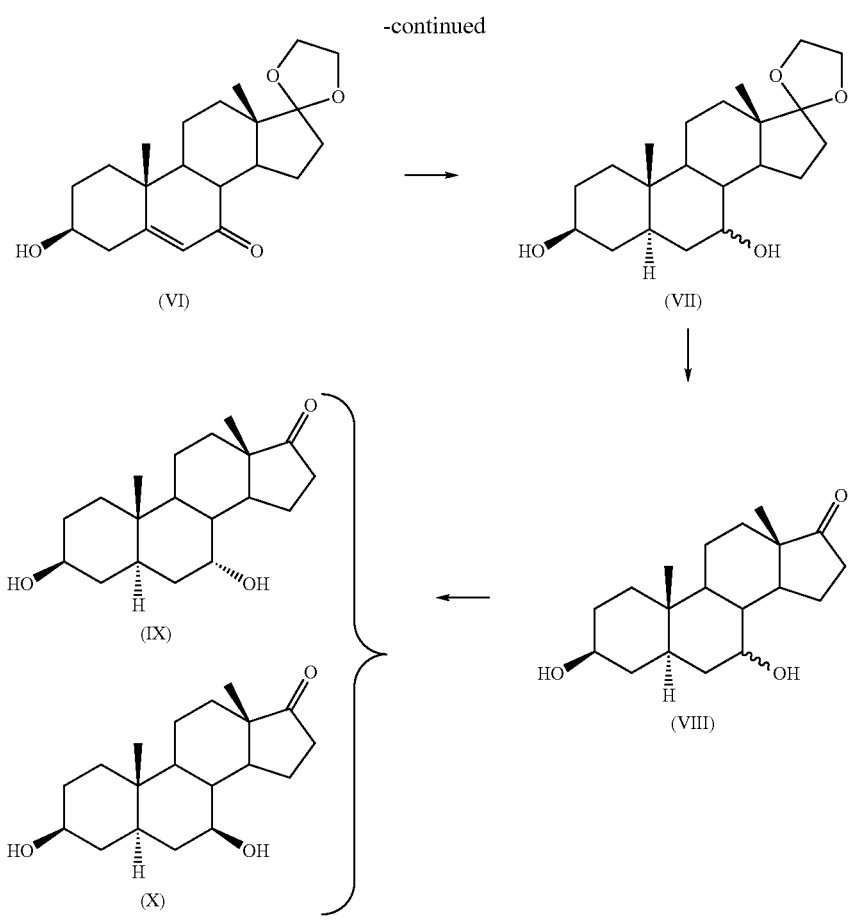

In this reaction scheme, DHEA (II) is acetylated to give the corresponding acetate of formula (III), which is then reacted with ethylene glycol, to give the ketal of formula (IV). The ketal (IV) is then oxidised as described in Example 3, to give the corresponding 7-keto compound (V), which is then deacetylated, to give the compound of formula (VI). This is reduced, to give 7-hydroxy-17-ketal-EPIA of formula (VII), which is then treated with an acid to remove the ketal group and give 7-hydroxy-EPIA, which is finally separated into the 7β- and 7α-isomers by chromatography, to give 7α-hydroxy-EPIA (In and 7β-hydroxy-EPIA (X).

The compounds of the present invention may be applier to the patient if it is suspected that they are in danger of an ischaemic event especially a stroke or head injury, or if they are suspected of developing a chronic neurodegenerative disease, such as Alzheimer's disease or CIND, which may be facilitated by chronic sub-threshold brain ischaemia or by reduced neuronal energy production, such as is frequently observed in the ageing brain. Such prophylactic application may be exceedingly useful. However, it has also been demonstrated that the compounds of the present invention have useful activity, even if applied after an ischaemic event, but it will be appreciated that it is preferred to administer the compounds as soon as possible, in order to avoid as much neuronal degeneration as possible. In some circumstances it may be desirable to administer repeated doses, especially where the patient remains in danger of an ischaemic event.

Suitable methods of administration are generally by injection, in order to achieve the desired result as soon as possible.

Thus, intravenous injection is particularly preferred but, in some circumstances it may be preferable to administer the compound directly into the cerebrospinal fluid.

The dose of the compound of the present invention will vary depending upon many factors, including the age, body weight and general condition of the patient, as well as the mode, frequency and route of administration. However, a dose of from 0.01 to 50 mg/kg body weight is generally recommended, a dose of from 0.05 to 20 mg/kg body weight being more preferred. This may be administered in a single dose or in divided doses.

The invention is further illustrated by the following non-limiting Examples, of which Examples 1 to 7 illustrate the preparation of compounds of the present invention and Examples 8 and 9 illustrate their activity. In Examples 1 to 7, the Roman numerals refer to the formulae in the reaction schemes shown above.

EXAMPLE 1

DHEA-3-acetate (III)

A solution of 50 ml of pyridine and 50 ml of acetic anhydride containing 10 g of DHEA (II) (34.72 mmol) was heated to reflux for 4 hours. The reaction medium was cooled, poured into water and extracted with ethyl acetate. The organic phase was dried over anhydrous sodium sulphate and evaporated to dryness. 11.0 g of DHEA-3-acetate (III) (33.33 mmol, 96%), which was recrystallised from ethanol, were obtained.

EXAMPLE 2

17-Ketal-DHEA-3-acetate (IV)

A solution of 100 ml of toluene containing 5 g of DHEA-3-acetate (III) (15.15 mmol), 5 ml of ethylene glycol and a catalytic amount of p-toluenesulphonic acid was heated to reflux with steam distillation using a Dean-Stark apparatus for 24 hours. The reaction medium was poured into 100 ml of a 10% w/v aqueous potassium carbonate solution. The organic phase was decanted. The aqueous phase was extracted with ethyl acetate. The organic phases were combined and evaporated to dryness. 5.10 g of 17-ketal-3-DIEA-acetate (IV) (13.64 mmol, 90%), which was recrystallised from ethanol, were obtained.

EXAMPLE 3

7-Keto-17-ketal-DHEA-3-acetate (V)

A solution of 70 ml of pyridine containing 5 g of 17-ketal-DHEA-3-acetate (IV) (13.37 mmol) and a catalytic amount of Bengal Rose was irradiated using a medium-pressure mercury vapour lamp with oxygen sparging. A catalytic amount of copper acetate was added to the reaction medium after 24 hours. The reaction medium, after 24 hours, was evaporated to dryness. The residue was purified by flash chromatography ($SiO_2$/ethyl acetate:cyclohexane 3/7). 3.11 g of 7-keto-17-ketal-DHEA-3-acetate (V) (8.02 mmol, 60%) were obtained.

EXAMPLE 4

7-Keto-17-ketal-DHEA (VI)

A solution of 50 ml of methanol containing 1% of potassium hydroxide and 1 g of 7-keto-17-ketal-DHEA-3-acetate (V) (2.58 mmol) was heated to reflux for 2 hours. The reaction medium was then cooled, neutralised and then extracted with ethyl acetate. The organic phase was dried over anhydrous sodium sulphate and then evaporated to dryness. 802 mg of 7-keto-17-ketal-DHEA 5 (2.32 mmol, 90%), which was recrystallised from methanol, were obtained.

EXAMPLE 5

7-Hydroxy-17-ketal-EPIA (VII)

10 g of 7-keto-17-ketal-DHEA (VI) (28.90 mmol) were added to a liquid ammonia solution at −33° C. containing 2.65 g of sodium. After 4 hours, ammonium chloride was added until the blue colour disappeared. 2.65 g of sodium were then added. After 4 hours, ammonium chloride was again added until the blue colour disappeared. Water was added and the ammonia was allowed to evaporate. The reaction medium was extracted with ethyl acetate. The organic phase was dried over anhydrous sodium sulphate and then evaporated to dryness. 6.07 g of 7-hydroxy-17-ketal-EPIA CM (17.34 mmol, 60%) were obtained.

EXAMPLE 6

7-Hydroxy EPIA (VIII)

A solution of 100 ml of acetone containing 5 ml of water, 10 g of 7-hydroxy-17-ketal-EPIA (VII) (28.57 mmol, 50%) and a catalytic amount of p-toluenesulphonic acid was heated to reflux for 4 hours. The reaction medium was cooled, poured into 100 ml of a 10% w/v aqueous sodium carbonate solution and then extracted with ethyl acetate. The organic phase was dried over anhydrous sodium sulphate and then evaporated to dryness. The residue was purified by flash chromatography ($SiO_2$/ethyl acetate). 5.24 g of 7-hydroxy-EPIA (VIII) (17.14 mmol, 60%) were obtained.

EXAMPLE 7

7α-Hydroxy-EPIA (IX) & 7β-hydroxy-EPIA (X)

7-Hydroxy-EPIA (VIII) (5 g) containing 7α and 7β epimers in a ratio 65/35 was purified by flash chromatography ($Al_2O_3$/$CHCl_3$). 7β-Hydroxy-EPIA (X) (2.5 g) was obtained first, before 7α-hydroxy-EPIA (IX) (1.34 g). 7β-Hydroxy-EPIA (X) and 7 cc-hydroxy-EPIA (IX) were recrystallised from ethyl acetate.

EXAMPLE 8

Protocol for Studying Hypoxic Neuronal Damage

Organotypic hippocampal slice cultures were prepared using the basic method of Pringle et al (1996, 1997) modified as follows:

Wistar rat pups (8-11 days old) were decapitated and the hippocampus rapidly dissected into ice-cold Gey's balanced salt solution supplemented with 4.5 mg/ml glucose. Slices were separated and plated onto Millicell CM culture inserts (4 per well) and maintained at 37° C./5% $CO_2$ for 14 days. Maintenance medium consisted of 25% heat-inactivated horse serum, 25% Hank's balanced salt solution (HBSS) and 50% minimum essential medium with added Earle's salts (MEM) supplemented with 1 mM glutamine and 4.5 mg/ml glucose. Medium was changed every 3-4 days.

Experimental hypoxia was performed as described previously (Pringle et al., 1996; 1997). Briefly, cultures were transferred to serum free medium (SFM—75% MEM, 25% HBSS supplemented with 1 mM glutamine and 4.5 mg/ml glucose) containing 5 μg/ml of the fluorescent exclusion dye propidium iodide (PI). Cultures were allowed to equilibrate in SFM for 60 minutes prior to imaging. PI fluorescence was detected using a Leica inverted microscope fitted with a rhodamine filter set. Any cultures in which PI fluorescence was detected at this stage were excluded from further study. Hypoxia was induced by transferring cultures to SFM (+PI) which had been saturated with 95%$N_2$/5%$CO_2$. Culture plates (without lids) were then sealed into an airtight chamber in which the atmosphere was saturated with 95%$N_2$/5%$CO_2$ by continuously blowing through gas at 10 L/min for ten minutes before being sealed and placed in the incubator for 170 mins (total time of hypoxia was therefore 180 mins). At the end of the hypoxic period cultures were returned to normoxic SFM containing PI and placed back in the incubator for 24 hours.

Neuronal damage was assessed as described previously (Pringle et al., 1996; 1997) using either NIH Image 1.60 running on an Apple IIsi computer or OpenLab 2.1 (Improvision) running on a Macintosh G4/400. Images were captured using a monochrome camera and saved onto optical disk for offline analysis. Light transmission images were captured prior to the addition of drugs, and PI fluorescence images recorded at the end of the 24-hour post-hypoxia recovery period. The area of the CA1 cell layer was determined from the transmission image. The area of PI fluorescence in CA1 was measured using the density slice function within NIH image or Openlab, and neuronal damage expressed as the percentage of the CA1 in which PI fluorescence was detected above background.

Steroid compounds were prepared by making an initial 1 mg/ml solution in ethanol and further diluting down in SFM. Compounds were added to the cultures for 45 minutes prior to hypoxia, during the hypoxic episode and during the post-hypoxic recovery period. Control experiments consisted of cultures treated with vehicle alone.

Results

Experiment 1:

An initial experiment was performed to determine whether 7βOH-EPIA and 7βOH-EPIA were neuroprotective at a high concentration of 100 nM. Hypoxia produced a lesion in 25.5±6.4% of CA1. This damage was significantly reduced by both 7αOH-EPIA and 7βOH-EPIA when present pre-, during and post-hypoxia as shown in Table I, below.

TABLE 1

| Compound | N | % Damage in CA1 |
| --- | --- | --- |
| Control Hypoxia | 17 | 25.5 ± 6.4 |
| Hypoxia + 100 nM 7αOH-EPIA | 16 | 4.0 ± 2.9** |
| Hypoxia + 100 nM 7βOH-EPIA | 16 | 9.0 ± 4.7* |

Experiment 2:

Having determined that both the α- and β-isomers of 7OH-EPIA were neuroprotective, we assessed the concentration-dependency of this effect. Control hypoxia resulted in neuronal damage to 31.9±4.7% of the CA1.7αOH-EPIA was significantly protective at 100 nM. A small, but not-statistically significant reduction, in neuronal damage was observed at 10 nM, and there was no effect at 1 nM. In contrast, 7βOH-EPIA was significantly neuroprotective at 10 nM and 100 nM, but activity was lost if the concentration was reduced to 1 nM. (See Table 2).

TABLE 2

| Compound | N | % Damage in CA1 |
| --- | --- | --- |
| Control Hypoxia | 29 | 31.9 ± 4.7 |
| Hypoxia + 1 nM 7αOH-EPIA | 14 | 28.8 ± 5.8 |
| Hypoxia + 10 nM 7αOH-EPIA | 15 | 21.9 ± 8.1 |
| Hypoxia + 100 nM 7αOH-EPIA | 16 | 11.8 ± 2.8** |
| Hypoxia + 1 nM 7βOH-EPIA | 15 | 20.6 ± 7.2 |
| Hypoxia + 10 nM 7βOH-EPIA | 12 | 11.9 ± 4.7* |
| Hypoxia + 100 nM 7βOH-EPIA | 13 | 14.3 ± 5.0* |

EXAMPLE 9

Global Cerebral Ischemia in Rats (4 Vessel Occlusion)

Cerebral ischemia was induced by four-vessel-occlusion (4VO) in male Wistar rats (250-280 g). Both vertebral arteries were occluded by electrocauterization in pentobarbital anesthesia (60 mg/kg i.p.). The animals were allowed to recover for 24 hours with free access to water but not food. The next day the carotid arteries were exposed under 2% halothane in 30% oxygen/70% nitrous oxide anesthesia and were occluded for 10 minutes using microvascular claps. Subsequently, both clamps were removed and both arteries were inspected for immediate reperfusion. During the operation and the following 3 hours normothermia of the animals (37.5Γ0.5° C.) was maintained by using a thermostatically controlled heating blanket connected to a rectal thermometer. For control, in sham-operated animals both vertebral arteries were cauterized in pentobarbital anesthesia and both common carotid arteries were exposed but not clamped under 2% halothane in 30% oxygen/70% nitrous oxide anesthesia the following day. The wound was treated with lidocaine gel and then sutured. The animals were kept under a heating lamp at 30° C. environmental temperature until they regained consciousness.

Seven groups of animals were investigated:
1. (n=8) steroid compound, 7β-OH EPIA (0.1 mg/kg, i.v. via tail vein, three injections: 15 minutes prior to the induction of ischemia, during ischemia and 5 minutes after reperfusion);
2. (n=8) steroid compound, 7β-OH EPIA (0.3 mg/kg, i. v. three injections as described in 1.);
3. (n=8) steroid compound, 7β-OH EPIA (1 mg/kg, i. v., three injections as described in 1.);
4. (n=8) NBQX (disodium salt, because more water soluble) as reference substance and positive control (TOCRIS, Germany, 30 mg/kg, i. p., three injections as described in 1.);
5. (n=8) received vehicle (0.9% NaCl, containing 100 μl Ethanol) three injections as described in 1.);
6. (n=8) ischemia alone;
7. (n=8) sham operated controls.

NBQX is 2,3-dihydroxy-6-nitro-7-sulfamoyl-benzo(F)quinoxaline and is known to have neuroprotective activity [Gill, R., Nordholm, L., Lodge D.: The neuroprotective action of 2,3-dihydroxy-6-nitro-7-sulfamoyl-benzo(F)quinoxaline (NBQX) in a rat focal ischaemia model. Brain Res. 580, 35-43, 1992].

7β-OH EPIA is 7β-hydroxyepiandrosterone, a compound of the present invention.

The substances were dissolved in 100 μl Ethanol and finally diluted with 0.9% NaCl.

After a survival time of 7 days after ischemia, all animals were perfusion fixed transcardially with 4% paraformaldehyde. The brains were then removed carefully and postfixed in the same fixative for 2 hours. After cryoprotection in 30% sucrose, the brains were rapidly frozen in isopentane and stored at −80° C. Twenty-micrometer cryostat sections comprising the hippocampal formation were Nissl stained with toluidine blue or NeuroTrace fluorescence.

Data Analysis:

The severity of neuronal damage in the hippocampal CA1 region after ischemia was evaluated by the number of surviving neurons using Nissl staining. The mean number of morphologically intact neurons per 400 μm length was calculated in CA1 region for each group. Cell counting was performed in 3-5 serial sections per animal and 6 times 400 μm CA1 area per section using a light microscope equipped with a 20× objective. The data were statistically analyzed by paired Student's t-test. Data were presented as mean±SEM.

Results and Discussion

Figure 1B:
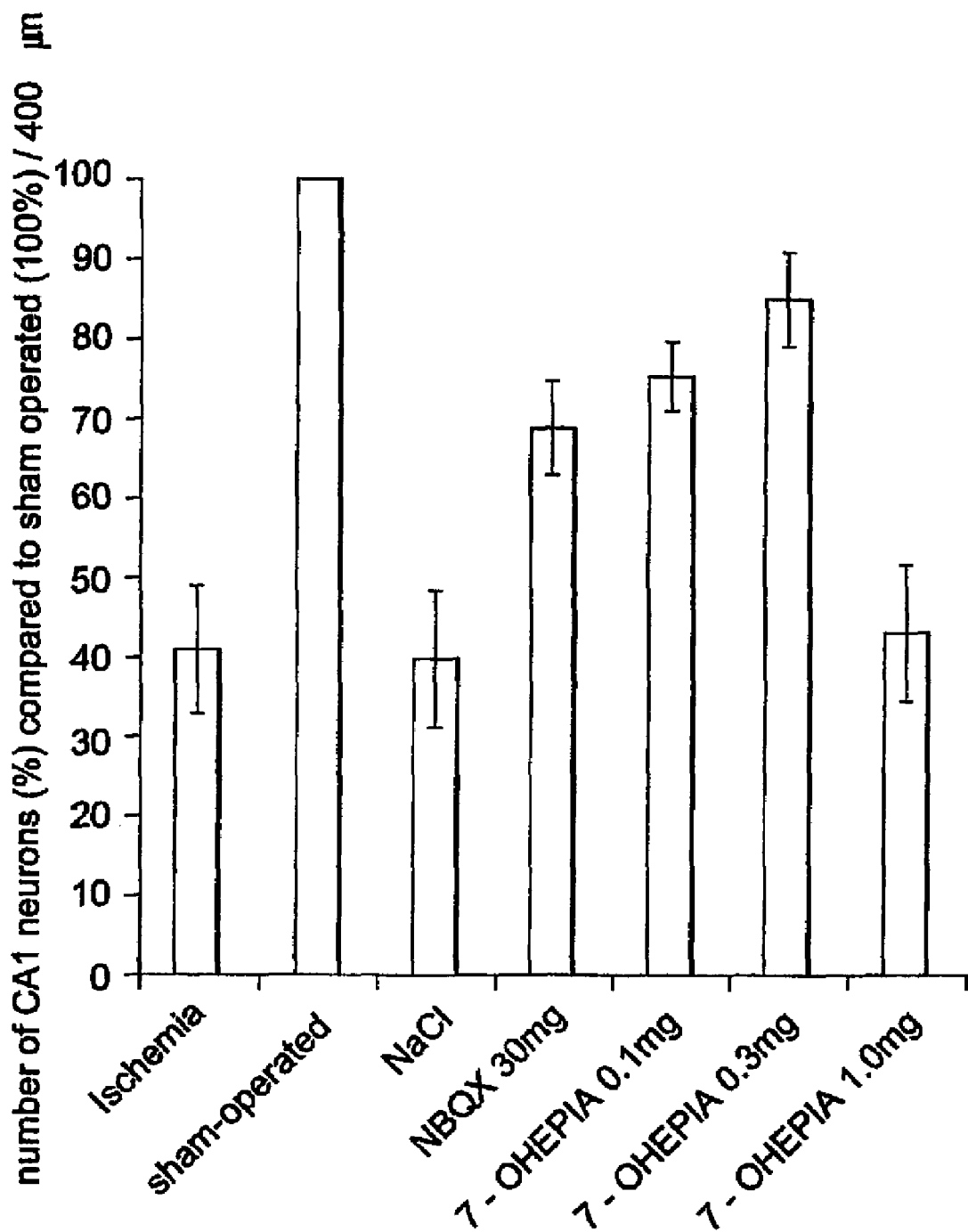
Figure 1C:
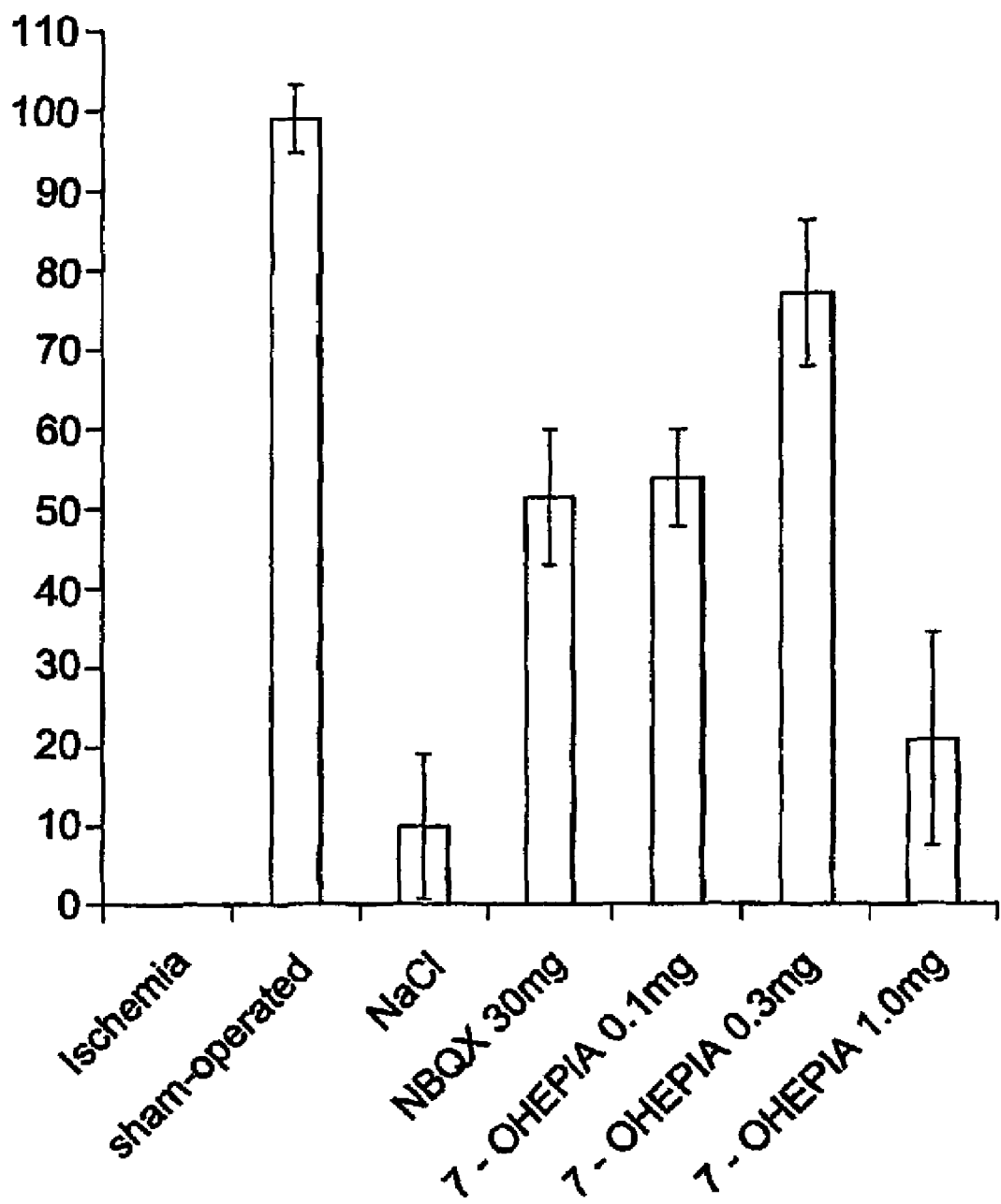

The results are shown in FIGS. 1A, 1B, and 1C of the accompanying drawings.

Morphological intact hippocampal CA1 neurons were characterized by Nissl staining (toluidine blue and NeuroTrace) with the following criteria: clear shape of a neuronal perikarya, large nucleus with a positive labeled nucleolus, a small cytoplasm zone around the nucleus with positive Nissl staining, indicating the intact rough endoplasmic reticulum with ribosomes and therefore the intact protein synthesis machinery.

10 minutes of global ischemia (mild ischemia) and a survival time of 7 days leads to a neurodegeneration of pyramidal cells selectively in the hippocampal CA1 region (FIGS. 1A-1C). The mean number of pyramidal cells in CA1 of sham operated animals was 121.5Γ4.3 (set as 100%). Therefore, 60% of CA1 neurons died after 10 minutes of global ischemia (FIG. 1B). The number of neurons in the animal group of ischemia and i. v. injection of vehicle (NaCl plus 100 µl Ethanol) applied as described in the experiment was comparable to that of the ischemia group alone (FIGS. 1A, 1B). NBQX (30 mg/kg, i.v., three injections as described in the experiment) showed a significant (p=0.03) neuroprotection in CA1 pyramidal cells compared to the ischemia group. Compared to the ischemia alone NBQX leads to a 47.5% neuroprotection while compared to the sham operated animals the protective effect was 68.5%. The neuroprotection caused by NBQX was in agreement with Gill et al., 1992 and Gill 1994 demonstrating the validity of the global ischemia model we used in our experiments. 7β-OH EPIA leads to a concentration dependent neuroprotection of hippocampal CA1 pyramidal cells after 10 minutes of global ischemia and a survival time of 7 days (FIG. 1A). T-test analysis revealed a highly significant neuroprotective effect of 7β-OH EPIA in concentrations of 0.1 mg/kg (p=0.01) and 0.3 mg/kg (p=0.0008). Compared to the sham operated group 7β-OH EPIA showed a 74.8% (0.1 mg/kg) and a 83.9% (0.3 mg/kg) neuroprotective effect on CA1 pyramidal cells, respectively (FIG. 1C). 7β-OH EPIA in a concentration of 1.0 mg/kg showed only a tendency to neuroprotection, but the effect was not significant.

In all experiments with 7β-OH EPIA injected i.v. prior, during and after ischemia we never observed any behavioral abnormalities of the animals.

The invention claimed is:

1. A method of treating neuronal damage in a mammal comprising administering thereto an effective amount of 7β-hydroxyepiandrosterone.

2. The method according to claim 1, wherein the neuronal damage is caused by stroke or brain trauma.

3. The method according to claim 1, wherein the neuronal damage is caused by Alzheimer's Disease, Parkinson's Disease, Cognitive Impairment No Dementia, spinal cord injury, or peripheral nerve injury.

4. A method for reducing neuronal cell death following acute neuronal damage in a mammal comprising administering thereto an effective amount of 7β-hydroxyepiandrosterone.

5. The method according to claim 4, wherein the acute neuronal damage is caused by stroke.

6. The method according to claim 4, wherein the acute neuronal damage is caused by spinal cord injury.

7. A method for reducing neuronal cell death following chronic neuronal damage in a mammal comprising administering thereto an effective amount of 7β-hydroxyepiandrosterone.

8. The method according to claim 7, wherein the chronic neuronal damage is caused by Alzheimer's Disease.

9. The method according to claim 7, wherein the chronic neuronal damage is caused by Parkinson's Disease.

* * * * *

UNITED STATES PATENT AND TRADEMARK OFFICE
CERTIFICATE OF CORRECTION

PATENT NO. : 7,718,639 B2
APPLICATION NO. : 10/312533
DATED : May 18, 2010
INVENTOR(S) : Ernst Wülfert et al.

It is certified that error appears in the above-identified patent and that said Letters Patent is hereby corrected as shown below:

In column 1, lines 4-5, "This application is a 371 of PCT/GB01/2937 filed Jun. 29, 2001" should read --This application is the 371 national phase of Int'l App. No. PCT/GB01/02937, filed June 29, 2001, which claims priority under 35 U.S.C. §§ 365(b) and 119(a)-(d) to foreign application no. GB0016022.6, filed June 29, 2000.--

Signed and Sealed this

Ninth Day of November, 2010

David J. Kappos
*Director of the United States Patent and Trademark Office*